(12) United States Patent
Keller et al.

(10) Patent No.: US 10,098,788 B2
(45) Date of Patent: Oct. 16, 2018

(54) ELECTRO-OPTICAL GLARE-PROTECTION FILTER WITH A LIQUID CRYSTAL CELL BEING A FRINGE-FIELD SWITCHING CELL FOR A WELDER PROTECTION DEVICE

(71) Applicant: Optrel AG, Wattwil (CH)

(72) Inventors: Leo Keller, Rueti ZH (CH); Martin Esposito, Rapperswil (CH)

(73) Assignee: Optrel Holding AG, Appenzell (CH)

( * ) Notice: Subject to any disclaimer, the term of this patent is extended or adjusted under 35 U.S.C. 154(b) by 0 days.

(21) Appl. No.: 15/538,304

(22) PCT Filed: Dec. 21, 2015

(86) PCT No.: PCT/EP2015/080834
§ 371 (c)(1),
(2) Date: Jun. 21, 2017

(87) PCT Pub. No.: WO2016/102492
PCT Pub. Date: Jun. 30, 2016

(65) Prior Publication Data
US 2017/0360612 A1 Dec. 21, 2017

(30) Foreign Application Priority Data
Dec. 22, 2014 (CH) .................................... 2012/14

(51) Int. Cl.
*A61F 9/06* (2006.01)
*G02F 1/1335* (2006.01)
*G02F 1/1343* (2006.01)

(52) U.S. Cl.
CPC ........ *A61F 9/067* (2013.01); *G02F 1/133502* (2013.01); *G02F 1/134363* (2013.01);
(Continued)

(58) Field of Classification Search
CPC ............... A61F 9/067; G02F 1/133502; G02F 1/134363
See application file for complete search history.

(56) References Cited

U.S. PATENT DOCUMENTS

| 2007/0070282 A1 | 3/2007 | Shibahara et al. |
| 2008/0068521 A1 | 3/2008 | Cottier |

OTHER PUBLICATIONS

The International Search Report and the Written Opinion of the International Searching Authority dated Mar. 11, 2016 in the corresponding international application No. PCT/EP/2015/080834.

(Continued)

*Primary Examiner* — Joseph L Williams
(74) *Attorney, Agent, or Firm* — Posz Law Group, PLC

(57) ABSTRACT

The electro-optical glare protection filter includes a liquid crystal cell, which is a laterally extended liquid crystal cell defining a volume between two laterally extended sides. The volume containing liquid crystals and having, in a vertical direction perpendicular to lateral directions, a thickness being smaller than an extension of the volume in any lateral direction. The FFS cell includes a first electrode structure and a second electrode structure, which are arranged to change an orientation of the liquid crystals in the volume when a voltage is applied between them. Both the first and the second electrode structure are present at the same laterally extended side of the volume. The first electrode structure may include a plurality of electrically separate electrodes, and the second electrode structure may include a plurality of electrode lines.

21 Claims, 6 Drawing Sheets

(52) U.S. Cl.
CPC ............ *G02F 2001/134372* (2013.01); *G02F 2201/124* (2013.01); *G02F 2203/66* (2013.01)

(56) References Cited

OTHER PUBLICATIONS

The International Preliminary Report on Patentability mailed by the International Bureau of WIPO dated Jul. 6, 2017 in the corresponding international application No. PCT/EP/2015/080834.

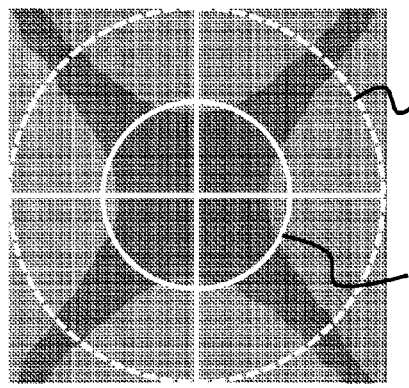
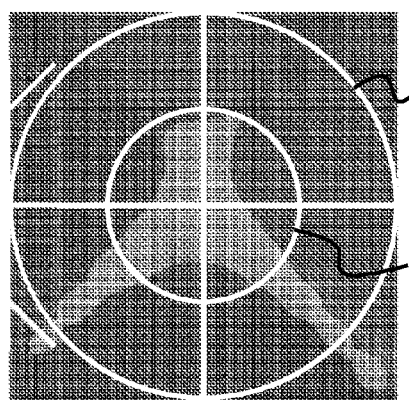
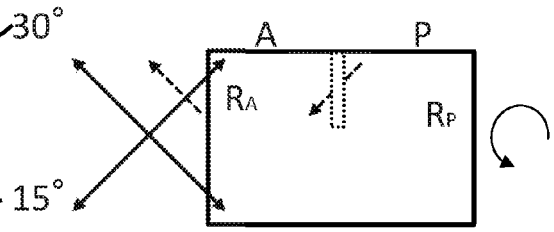
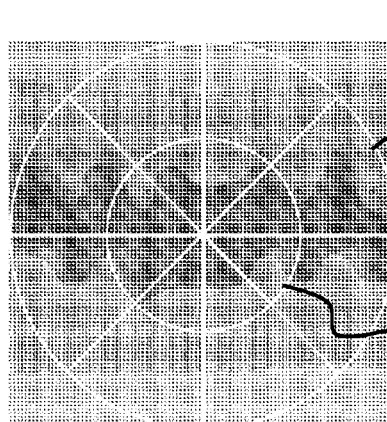
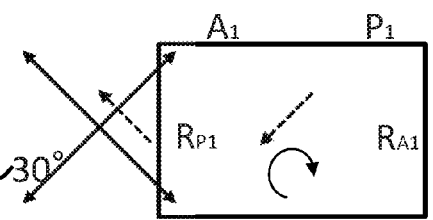
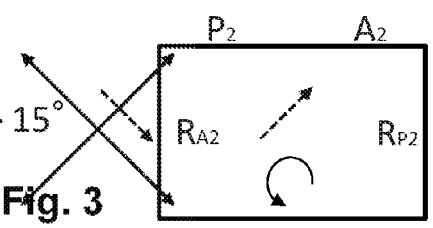
Fig. 1  Fig. 1a
Fig. 2  Fig. 2a
Fig. 3  Fig. 3a  Fig. 3b

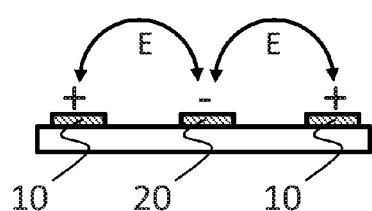 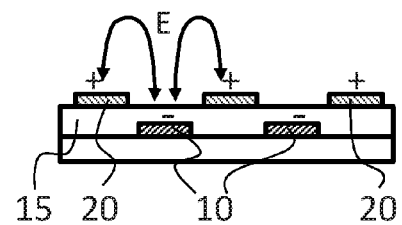
Fig. 8a  Fig. 8c
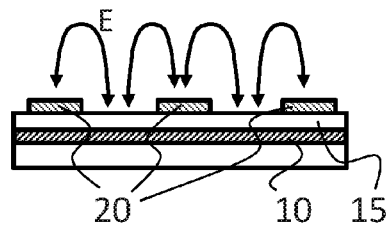
Fig. 8b
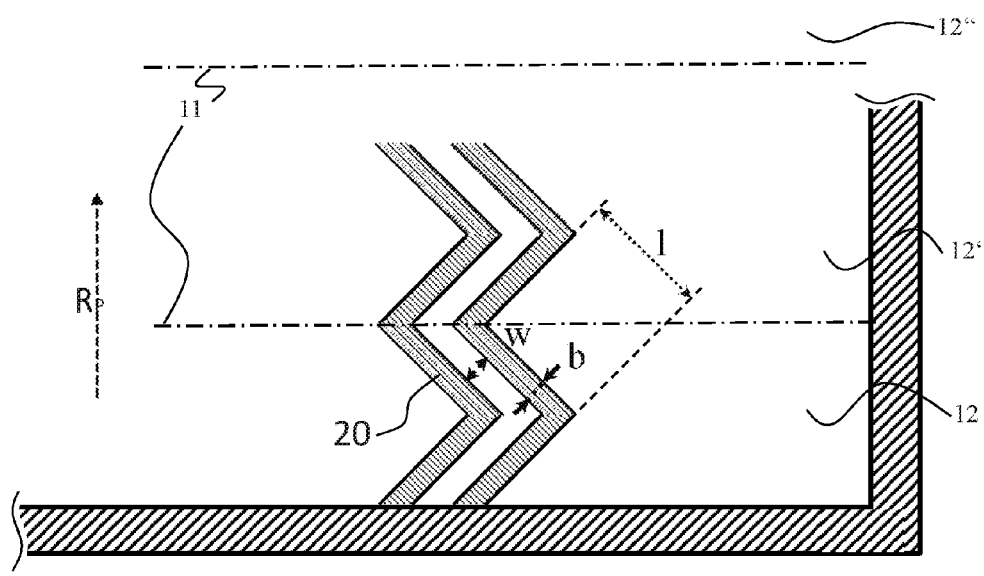
Fig. 9

ELECTRO-OPTICAL GLARE-PROTECTION FILTER WITH A LIQUID CRYSTAL CELL BEING A FRINGE-FIELD SWITCHING CELL FOR A WELDER PROTECTION DEVICE

CROSS REFERENCE TO RELATED APPLICATIONS

This application is a U.S. national stage application of PCT/EP2015/080834 filed on Dec. 21, 2015, which is based on Swiss Patent Application No. 02012/14 filed on Dec. 22, 2014, the contents of which are incorporated herein by reference.

The invention relates to the field of glare protection, such as is used e.g. in protective masks or protective helmets for welders and in particular to an electro-optical glare protection filter as well as a glare protection unit for a portable glare protection device. It relates to devices according to the preambles of the corresponding independent claims.

Glare protection units for portable glare protection devices such as protective masks and protective goggles are generally known. Modern glare protection devices comprise electro-optical filters, e.g. with a liquid crystal element, the transmittance of which is adapted automatically or manually. This kind of filter may possess a predetermined or, optionally, an adjustable protection level, and shall usually have a level of protection which is as little as possible dependent on the viewing angle.

WO 2004/102265 has the object to achieve a symmetrical dependency on angle of view in relation to the perpendicular to the LCD-element of a glare protection filter. The dependency on angle of view is ascribed to the positive optical anisotropy of the birefringence in the LCD-cell. It is compensated by using a negatively birefringent compensation layer. For an optimum effect, the parameters of the cell and the compensation layer must be matched to each other, and the cell must be an HT (highly twisted) cell and if possible only let a single light propagation mode of light pass.

U.S. Pat. No. 5,515,186 describes a protective mask for welders with arrangements of polarizers, which are matched to each other such that a region, which appears to be brighter in a combination of two polarizers, is darkened again in combination with a further polarizer. The liquid crystal cells are specifically of a type which functions on the principle of variable optical retardation, as opposed to "twisted nematic" or TN cells, in which the polarization is twisted. According to U.S. Pat. No. 5,515,186 a polarization angle other than 90° may be chosen, in order to compensate a residual birefringence, such that a maximal contrast is achieved at an angle of view perpendicular to the cells.

WO 95/29428 shows a glare protection filter with a combination of two liquid crystal cells in a mutually twisted arrangement, wherein the two liquid crystal cells are respectively arranged between two mutually obliterating polarization filters. The liquid crystal cells hereby consist of low twisted nematic (LTN) cells, as, e.g., disclosed in FR 2728358, U.S. Pat. Nos. 4,952,030 and 4,609,255.

WO 97/15255 describes one single or two liquid crystal cells, the polarizers of which are arranged to mutually extinguish one another, that is, to be in perpendicular to one another respectively. In addition, a retardation film is arranged between the two polarizers in such way that the fast axis of the retardation means deviates from the fast axis of the inherent retardation of the cell for reducing the dependence on angle of view. Further prior art documents on liquid crystal cells are, e.g., U.S. Pat. Nos. 5,940,155, 7,884,888 B2, US 2012/0002121 A1.

One object of the invention is to create a new type of liquid crystal (LC) based electro-optical glare protection filters.

In particular, such protection filters shall be provided which exhibit a low dependency on angle of view of the provided protection. In other words, the protection filters shall have an opacity which has a relatively low dependency on the polar angle.

Another object of the invention is to provide such protection filters which are capable of providing a particularly high degree of opacity, at least if so desired.

Another object of the invention is to provide such protection filters which have a particularly high light efficiency.

Further objects emerge from the description and embodiments below.

At least one of these objects is at least partially achieved by apparatuses according to the patent claims.

The electro-optical glare protection filter comprises a liquid crystal cell (LC cell) referred to as first cell, wherein the first cell is an FFS cell, wherein an FFS cell is defined as follows: It is a laterally extended liquid crystal cell defining a volume between two laterally extended sides, the volume containing liquid crystals (LCs) and having, in a vertical direction perpendicular to lateral directions, a thickness being smaller than an extension of the volume in any lateral direction, the FFS cell comprising a first electrode structure and a second electrode structure, which are arranged to change an orientation of the liquid crystals in the volume when a voltage is applied between them, wherein both, the first and the second electrode structure, are present at the same laterally extended side of the volume.

Thus, one can say that the two electrode structures are located at the same laterally extended side of the first cell.

Typically, the first cell is structured and configured for normally-white (NW) operation.

In simple words, one could roughly sketch an FFS cell as an LC cell having both electrodes (more precisely: both electrode structures) on the same side, wherein that side is one of the two large sides of the LC cell.

In the literature, FFS cells are also known as "fringe-field switching" LC cells and also as "in-plane switching" LC cells. But the terms are not used consistently in the literature. Furthermore, "fringe-field switching" LC cells and "in-plane switching" LC cells are sometimes distinguished from each other, namely with respect to the more detailed arrangement of the electrodes. Accordingly, we have introduced and defined the term "FFS cell" used in the present patent application, in order to avoid misinterpretations.

However, as will become clear, it is envisaged to provide an LC cell operable in an in-plane switching mode, i.e. such that when switching from an off-state to an on-state of the LC cell (or vice versa), the director of the LCs changes from one lateral direction to another lateral direction, i.e. the director remains aligned (substantially) along a lateral direction, while the lateral direction in the two states is not the same.

For the sake of completeness we note that the director of an LC is a vector pointing along the length of the elongated LC molecule, wherein the direction or sign of the director is of no importance.

And furthermore, it will become clear that the envisaged FFS cell is intended to rely, for achieving a switching from a "white state," i.e. transparent state, to a "black state," i.e. non-transparent state, (or vice versa), on a birefringence of the LCs, i.e. on $\Delta n$ being different from zero. Therein, $\Delta n = n_e - n_o$ being the difference between the index of refraction $n_o$ for ordinarily polarized light having a polarization axis of the E vector aligned perpendicularly to the director and the index of refraction $n_e$ for extraordinarily polarized light having a polarization axis of the E vector aligned parallel to the director.

In particular, cell gap width d and Δn of the LCs are selected such that the phase retardation approximation π d Δn/λ equals a fraction of π (corresponding to a fraction of 180°) for wavelengths λ of visible light for which purpose wavelengths λ of between 400 nm and 780 nm, in particular 550 nm are assumed. For achieving an overall phase retardation of π or of a multiple of π, typically, further retarders are introduced, so as to complement said fraction of π to π or to said integer multiple of π. Typical values for Δn are in a range of 0.06 to 0.25. Typical values for d are in a range of 2 μm to 8μm.

As is the case also for known LC cells, in reaction to an application of different electric potentials to the first electrode structure and the second electrode structure, an alignment of the LCs can be achieved and changed, so as to switch between the transparent white state and the non-transparent black state when switching from a zero potential difference to a driving voltage (which corresponds to "normally white" operation and, accordingly, to a "NW cell"). In "normally black" cells (NB cells), polarizer and analyzer are crossed, i.e. at 90°, such that in off-state (no driving voltage applied), light transmission is blocked.

With respect to the current invention, NW cells (normally-white liquid crystal cells) are preferred, since a fast darkening of the filter is better achieved by application of a voltage than by switching off a voltage, in particular if initially, a pulse of an overdriving voltage larger than the (long-term applicable) driving voltage is applied.

Driving voltages for LC cells are usually alternating voltages, in particular square-wave voltages. 40 Hz is a typical frequency for driving voltages.

An FFS cell usually comprises a first and a second transparent plate such as two glass plates aligned in parallel, by means of which the two laterally extended sides are defined. Both, the first and the second electrode structures, are present at the first transparent plate, then.

In prior art LC cells, one of the two electrodes is often referred to as "common" and the other simply as "electrode", wherein the first electrode structure can roughly be identified with the "common" and the second electrode structure can roughly be identified with the "electrode". However, the first and second electrode structures may differ considerably from prior art "common" and "electrode" structures.

One can propose that a liquid crystal cell has or defines a cell plane, namely the plane through which light passes through the liquid crystal cell or is blocked from passing through liquid crystal cell, depending on the application of voltages to the electrode structures of the liquid crystal cell. That cell plane then defines what is meant to be a lateral plane.

For the filter, the thickness of the volume (in vertical direction, normal to the lateral plane and in particular the cell plane) is typically smaller by at least three, or rather by at least four, orders of magnitude than any lateral extension of the volume. Thus, such a filter is strongly different from an LC cell of a single pixel of a typical LC-based display.

In particular, the thickness of the volume (in vertical direction; also referred to as cell gap) is smaller than 10 μm, more particularly smaller than 8 μm.

The thickness of the volume (cell gap width d) may in particular be smaller than 6 μm and larger than 2 μm.

An extension of the volume in any lateral direction is typically at least 2 cm, in particular at least 5 cm.

For glare protection applications, the use of LC cells with a matrix of very many very small pixels, e.g., such as used in TV screen or similar applications, have the disadvantage of producing very much stray light.

The electrode material for the electrode structures is a conductive, transparent material, e.g., ITO (indium tin oxide). Transparent electrode materials, such as Graphene, may be used as alternative electrode material.

In particular, the electrode material may be index-matched (with the material adjacent to the the electrodes such as glass or transparent polymer material).

In particular, the electrode material has an refractive index between 1.4 and 1.6.

In contrast to LC cells used in customary pixel-based displays which have lateral extensions of between 1 μm and 10 μm, LC cells with lateral extensions as proposed for the filter may require special precautions in order to ensure sufficiently constant optical properties (laterally) across the filter. In particular, special precautions may have to be taken in order to achieve a sufficiently constant electric field distribution (laterally) across the filter.

Therefore, in one embodiment, the first electrode structure comprises a plurality of electrically separate electrodes. Thus, the first electrode structure may comprise a set of separately operable electrodes. In particular, the first electrode structure may be considered a segmented electrode, i.e. an electrode composed of a plurality of electrode segments which may be held at different electrical potentials.

When connected to a drive circuit, at least a first set of the electrically separate electrodes is at an electrical potential different from an electrical potential at which a second set of the electrically separate electrodes is.

The provision of a first electrode structure comprising a plurality of electrically separate electrodes can make possible to apply close to edges and/or close to corners of the first cell a drive voltage which is higher than at an increased distance from the edge. Therein, the drive voltage is a voltage applied between the respective separate electrode and the second electrode structure.

In particular, the described first electrode structure comprising a plurality of electrically separate electrodes can make it possible to compensate for the decreasing field strengths caused by a high sheet resistance of elongated electrodes sections of the second electrode structure.

In one embodiment, a lateral area covered by the first electrode structure amounts to at least 90%, in particular at least 95%, of an area of any of the two laterally extended sides. Typically, even less than 0.5% of an area of any of the two laterally extended sides is not covered by the first electrode structure. In particular if combined with the above-described (quasi-) segmented electrode, this embodiment results in a nearly full-area first electrode structure comprising a plurality of electrically separate electrodes.

In one embodiment, the filter comprises a drive circuit for producing at least a first and a second drive voltage, wherein the drive circuit is connected to the first and second electrode structures for applying the first drive voltage between the second electrode structure and a first one of the plurality of electrically separate electrodes and for applying the second drive voltage between the second electrode structure and a second one of the plurality of electrically separate electrodes.

Therein, it may in particular be provided that a minimum drive voltage for application between any one of the electrically separate electrodes of the first electrode structure and the second electrode structure amounts to at least 2.4 V or, more particularly, to at least 6 V or even at least 12 V; and a difference between any two drive voltages applied between any one of the plurality of electrically separate electrodes and the second electrode structure amounts to at most 0.4 V, in particular to at most 8 V. Therein, of course, the first drive voltage is different from the second drive voltage, and the first one of the plurality of electrically separate electrodes is not identical with the second one of the plurality of electrically separate electrodes.

Therein, it may furthermore be provided that a difference between a drive voltage applied between the second electrode structure and any one of the plurality of electrically separate electrodes and a drive voltage applied between the second electrode structure and an adjacent one of the plurality of electrically separate electrodes amounts to less than 1.5 V, in particular to less than 0.8 V. In other words, the resulting voltage between adjacent ones of the plurality of electrically separate electrodes amounts to less than 1.5 V, in particular to less than 0.8 V.

Typically, when the filter shall be switched to its non-transparent state, firstly, a pulse of an overdriving voltage of typically at least 35 V, in particular at least 40 V is applied between the second electrode structure and any one of the plurality of electrically separate electrodes, e.g., for less than 0.1 ms. This can effect a very fast realignment of many of the LCs in the LC cell.

For achieving an improved polar angle contrast distribution in the on-state (usually corresponding to the black state), it may be of advantage to create in the on-state at least two, in particular exactly two types of domains, wherein the alignment direction of the LCs in domains of the two different domain types is different. In addition, a distribution of the two domain types (laterally) across the filter shall be quite fine, so as to avoid disturbing optical effects for a person using the filter. In the LC cell, usually at least $10^3$, typically at least $10^4$ or rather at least $10^5$ separate regions of first-type domains and of second-type domains are present in the LC cell.

It is suggested to achieve the formation of different domain types by suitably structuring the second electrode structure.

Accordingly, in one embodiment, the second electrode structure comprises an electrode comprising a multitude of areas of a first type and a multitude of areas of a second type, wherein each first-type area comprises a plurality of electrode sections of the second electrode structure which run along a first lateral direction, and wherein each second-type area comprises a plurality of electrode sections of the second electrode structure which run along a second lateral direction, different from the first lateral direction.

This way, a distribution over the lateral extension of the first cell of two domains of orientations of the liquid crystals can be created.

It may in particular be provided that for each of said areas, there exists a lateral direction in which the respective area extends along said lateral direction by at most 20 μm. This may reduce disturbing optical effects for a person looking through the filter.

It may be provided that the electrically separate electrodes of the first electrode structure are distanced from each other by separation lines. And moreover, the separation lines may be parallel to each other. And furthermore, an angle of at most 90° (i.e. an acute or right angle) formed between the separation lines and the first lateral direction may amount to at least 30°, and at most 60° (when projected into a common lateral plane, of course). And still furthermore, an angle of at most 90° formed between the separation lines and the second lateral direction may amount to at least 30° and to at most 60° (when projected into a common lateral plane, of course).

With reference to the "specific lateral direction" explained below, it may furthermore be provided that an angle of at most 90° formed between the separation lines and the specific lateral direction amounts to at least 60° and in particular to at least 80°. It may in particular, be a right angle.

In one embodiment, an angle between the first lateral direction and the second lateral direction amounts to between 60° and 120°, in particular to between 80° and 100°. It may in particular equal 90°.

It may also be provided that an acute angle between the first lateral direction and a rubbing direction of the first cell amounts to between 30° and 60° (more particularly to between 40° and 50°), and an acute angle between the second lateral direction and a rubbing direction of the first cell amounts to between 30° and 60° (more particularly to between 40° and 50°).

Rubbing and corresponding rubbing directions are well known in the art of LC cells; they provide a preferred alignment of the LCs near the rubbed sides of the volume, and in off-state, a default alignment of the LCs is provided by the rubbing.

Despite the terms rubbing and buffing originating from mechanical treatments, they shall not imply that the rubbing/buffing is indeed accomplished in a mechanical fashion. This is merely one possibility, but other possibilities may be applied. E.g., a polymer layer in the LC may be structured using light. The so-called photo-alignment allows to achieve a highly precise structuring such that a very precise alignment of the LCs located at the polymer layer is achieved.

In one embodiment, the second electrode structure comprises an electrode comprising a plurality of zigzag-shaped electrode lines which are aligned parallel to each other. This may be one way of obtaining a multi-domain LC cell; each of the the zigzag-shaped electrode lines runs along a straight line, and these straight lines are mutually parallel, namely parallel to a specific lateral direction.

In particular, the second electrode structure may comprise an electrode comprising a plurality of electrode lines each of which is composed of a multitude of like chevrons concatenated along a specific lateral direction. This is a more specific way of obtaining a multi-domain LC cell. E.g., more than 100 like (i.e. equally shaped) chevrons may be comprised in one of the electrode lines.

Even more particularly, the second electrode structure comprises an electrode comprising a plurality of electrode lines, wherein a first one of the electrode lines is obtainable by concatenating a multitude of parallel-aligned like chevrons along the specific lateral direction, and wherein the other electrode lines are obtainable by copying the first electrode line and shifting it in a lateral direction perpendicular to the first electrode line.

The shape of a chevron is described, e.g., by an angle bracket ("<"). In other words, a chevron is formed by two lines or bars, also called "legs" joined at their ends at an angle. The legs can be of the same length, which is typically the case; however, it is also possible that a chevron has legs of different length.

The legs of the chevrons may both in particular have an inclination angle φ (φ being, by definition an acute angle, that is, smaller than 90°) of between 30° and 60°, in particular 45°±5°, with respect to the specific lateral direction. Consequently, the angle between adjacent legs of the chevrons is twice the inclination angle φ.

Said specific lateral direction may also be considered a general electrode direction (about which the legs of the chevrons are meandering). Typically, the specific lateral direction is aligned parallel to a rubbing direction of the LC cell.

Despite the above, the electrode lines may, more generally, be composed of chevrons which are not all like chevrons, i.e. chevrons which are not congeneric, being not all equally shaped.

Each chevron usually consists of two mutually angled legs. Each of the legs usually is a straight section.

In one embodiment, for each chevron, a width of the legs of the chevron is between 0.1 µm and 3 µm.

In one embodiment, a gap width between neighboring electrode lines is between 0.5 µm and 4 µm. The gap width is meant to be a minimum distance measured perpendicularly to legs of chevrons.

In one embodiment, the legs have lengths of between one time and five times the width of the respective leg.

In one embodiment, the legs have lengths amounting to cell gap width d plus or minus 20%, in particular plus or minus 10%.

In one embodiment, an average length of the legs (i.e. the sum of the leg lengths of all chevrons, divided by the number of legs) amounts within 8% to cell gap width d.

In one embodiment, the first cell is anti-parallel rubbed and
in a first case: P-buffed and in E-Mode;
or is
in a second case: X-buffed and in O-Mode.

An FFS cell comprises, like most LC cells, a polarizer and an analyzer for blocking and letting pass light of a specific polarization. In an FFS cell, the transmission directions of the polarizer and the analyzer are aligned parallel to each other.

In a normally white (NW) FFS cell, the transmission directions of the polarizer and the analyzer are aligned parallel to each other. Under consideration of the above-described phase retardation approximation π d Δn/λ, it can be determined that a phase retardation of 180°, or an integer multiple of 180° (i.e., in radians, of an integer multiple of π), produces a rotation of the linear polarization plane of the light in the LC cell by exactly 90°, the latter making possible to switch from a bright state to a dark state in reaction to an application of an alternating electric field.

In a P-buffed cell, the rubbing direction (also referred to as buffing direction) is aligned parallel to the transmission direction of the polarizer. And in an X-buffed cell, the rubbing direction is aligned perpendicularly to the transmission direction of the polarizer.

In E-Mode (extraordinary mode), a polarization of light incident on the LCs is aligned parallel to the LC's director.

In O-Mode (ordinary mode), a polarization of light incident on the LCs is aligned perpendicularly to the LC's director.

The first and the second case are two ways of realizing an LC cell, wherein these two cases may be combined in a filter comprising two FFS cells (stacked in a vertical direction, a vertical direction being perpendicular to any lateral direction).

In one embodiment, the first case applies, and the above-described specific lateral direction is aligned parallel to a rubbing direction of the first cell. Typically, LCs having a negative dielectrical anisotropy (Δε<0) are used. However, alternatively, LCs may be used which have a positive dielectrical anisotropy (Δε<0).

In another embodiment, the second case applies, and the above-described specific lateral direction is aligned perpendicularly to the rubbing direction. Also in this case, LCs having a negative dielectrical anisotropy (Δε<0) are typically used. However, alternatively, LCs may be used which have a positive dielectrical anisotropy (Δε<0).

In one embodiment, the first electrode structure is electrically insulated from the second electrode structure by an electrically insulating layer present between them. The layer may in particular be a layer of a solid material.

It may be provided that the first and second electrode structures are arranged at the same distance to a first of the two laterally extended sides. This may be the case, e.g., if the first and second electrodes comprise interlacing electrode parts ("interdigital electrodes").

In one embodiment, the first cell comprises an electrically insulating layer, wherein the first electrode structure is located on a side of the layer facing away from the volume, whereas the second electrode structure is located on a side of the layer facing towards the volume, in particular wherein the first electrode structure is located at a distance from the volume larger than a distance of the second electrode structure from the volume.

This can make it possible to have electrode lines of the second electrode structures laterally closer to each other, which may lead to an increased portion of electric field components being aligned along lateral directions, and this again may lead to an increased of light efficiency.

An electrical field distribution in the volume particularly suitable for the filter may be obtainable this way.

In one embodiment, the liquid crystals in the first cell have a negative dielectrical anisotropy. This anisotropy may in particular amount to between −0.5 and −5.

A selection of such liquid crystals may make it possible to achieve a particularly high light efficiency.

In case that LCs with a positive dielectrical anisotropy are in the LC cell, their anisotropy may in particular amount to between +4 and +25.

Typically, LCs having a a positive dielectrical anisotropy make possible a faster switching. And on the other hand, LCs having a a negative dielectrical anisotropy tend to provide a better in-plane twist.

If LCs have a negative dielectrical anisotropy, their dielectrical anisotropy Δε is below zero, wherein Δε designates the difference between $\varepsilon_{par}-\varepsilon_{perp}$, wherein $\varepsilon_{par}$ designates the LC's dielectrical dipole moment for an electrical field component aligned perpendicular to the LC's director, and $\varepsilon_{perp}$ designates the LC's dielectrical dipole moment for an electrical field component aligned parallel to the LC's director.

However, it is also possible to use LCs having a positive dielectrical anisotropy (Δε>0).

In one embodiment, the first cell comprises, in addition, at least one retarding element, in particular at least one uniaxial retarder. For example, one or more a-plates may be provided. A positive retarder may be provided, and more particularly, a positive and a negative retarder, e.g., a positive a-plate and a negative a-plate may be provided.

A retardation value of the at least one retarding element may, e.g., amount to between 20 nm and 110 nm. E.g., a positive a-plate with a retardation value of between +60 nm and +100 nm and a a negative a-plate with a retardation value of between −60 nm and −100 nm may be provided.

The provision of one or more retarding elements can be taken for introducing an additional birefringence in the LC cell (in addition to the birefringence produced by the LCs), namely for achieving a phase retardation between the incoming linearly polarized light and the outgoing linearly polarized light of 180° (corresponding to half a wavelength of the light) than without the one or more retarding elements.

Furthermore, a compensation of birefringence introduced by polarizer and analyzer of the LC cell can be achieved by the at least one retarding element.

The choice of a positive retarder means that $n_e > n_o$ applies (extraordinary index of refraction larger than ordinary index of refraction; $n_o$ designating the refractive index for light travelling faster through a uniaxial material, $n_e$ designating the refractive index for light travelling slower through a uniaxial material, thereby producing a phase difference (phase retardation) leading to a different polarization state of the emerging light.

The retarding element may, e.g., be a film, e.g., located at one of the two laterally extended sides of the volume.

In one embodiment, the filter comprises, in addition, a liquid crystal cell referred to as second cell. In particular, the first and second cells may be stacked with their respective vertical directions coinciding. Accordingly, the two LC cells are stacked upon each other with their cell planes being parallel to each other.

This may on the one hand increase the degree of non-transparentness (opacity) and on the other hand lead to a more homogeneous contrast distribution (contrast in dependence of viewing angle through the filter).

In one embodiment, the filter comprises, in addition to the first and second cells, a liquid crystal cell referred to as third cell. In particular, the first, second and third cells may be stacked with their respective vertical directions coinciding. Accordingly, the three LC cells are stacked upon each other with their cell planes being parallel to each other.

In one embodiment, the second cell is a twisted nematic liquid crystal cell (TN cell).

Selecting a TN cell may make possible to achieve a particularly fast switching, i.e. to achieving a particularly short time within which the filter reaches a certain opacity.

A TN cell (which may optionally be an LTN cell) may be characterized by a twist angle of typically between 75° and 90°, wherein it may be operated (in E-mode or in O-mode) in a right- or left-hand adiabatic following, or wave-guiding mode, wherein the twist angle is equal to the Mauguin parameter $2\pi \cdot \Delta n \cdot d/\lambda$ and wherein the equation $d\Delta n/\lambda = 0.5 \sqrt{3}$ for the first minimum condition according to Gooch & Tarry applies. Therein, d designates the width of the cell gap, $\lambda$ designates the wavelength of the light involved, e.g., (approximately 550 nm) for visible light, and $\Delta n$ designates the birefringence of the LC.

In one embodiment, the second cell is an FFS cell. In this case, a particularly homogeneous contrast distribution may be achievable.

In this case, it is possible to provide that both, the LCs of the first cell and the LCs of the second cell, have a negative dielectrical anisotropy.

But it is also possible that the LCs of the first cell have a negative dielectrical anisotropy, while the LCs of the second cell have a positive dielectrical anisotropy.

A provision of LCs with a positive dielectrical anisotropy may shorten the switching time of the filter and/or may lower the required driving voltage of the filter. However, a lower light efficiency of the shutter may be another consequence of LCs with a positive dielectrical anisotropy.

Both, the first and the second cell, are usually NW cells.

If both, the first and the second cell, comprise second electrode structures making possible to produce two types of domains (the alignment of the LCs in domains of the two different domain types being different), it can be possible to produce a four-domain electro-optical glare protection filter. And such a filter may provide a particularly uniform contrast distribution.

In one embodiment with two FFS cells,
the first cell is anti-parallel rubbed and P-buffed and in E-Mode, wherein the second electrode structure of the first cell comprises an electrode comprising a plurality of electrode lines each of which is composed of a multitude of chevrons concatenated along a first common lateral direction;
the second cell is anti-parallel rubbed and X-buffed and in O-Mode, wherein the second electrode structure of the scond cell comprises an electrode comprising a plurality of electrode lines each of which is composed of a multitude of chevrons concatenated along a second common lateral direction;
wherein a rubbing direction of the first cell is perpendicular to a rubbing direction of the second cell, and wherein the first common lateral direction is parallel or perpendicular to the second common lateral direction.

In one embodiment, the first common lateral direction is parallel to the rubbing direction of the first cell. LCs having a negative dielectrical anisotropy will usually be present in the first cell. However, LCs having a positive dielectrical anisotropy may alternatively be used.

In one embodiment, which of course may be combined with the before-mentioned embodiment, the second common lateral direction is parallel to the rubbing direction of the second cell. LCs having a negative dielectrical anisotropy will usually be present in the second cell. In an alternative embodiment, the second cell comprises LCs having a positive dielectrical anisotropy.

In particular LC having a negative dielectrical anisotropy may be present in the first cell, while LC having a positive dielectrical anisotropy may be present in the second cell; or vice versa.

In the embodiment with two FFS cells, in particular at least one of the following is provided:
the perpendicular alignment of the rubbing direction of the first cell to the rubbing direction of the second cell deviates from 90° by an angle of between 1° and 8°;
the parallel alignment of a rubbing direction at a first of the two laterally extended sides of the first cell to a rubbing direction at a second of the two laterally extended sides of the first cell deviates from 0° by an angle of between 1° and 8°;
the parallel alignment of a rubbing direction at a first of the two laterally extended sides of the second cell to a rubbing direction at a second of the two laterally extended sides of the second cell deviates from 0° by an angle of between 1° and 8°;
a parallel alignment of a polarizing direction of a polarizer at a first of the two laterally extended sides of the first cell and a polarizing direction of an analyzer at a second of the two laterally extended sides of the first cell deviates from 0° by an angle of between 1° and 8°;
a parallel alignment of a polarizing direction of a polarizer at a first of the two laterally extended sides of the second cell and a polarizing direction of an analyzer at a second of the two laterally extended sides of the second cell deviates from 0° by an angle of between 1° and 8°.

Embodiments with slight deviations from the parallel (0°) and perpendicular (90°) alignment, respectively, may provide an improved polar contrast distribution compared to a precise alignment, respectively, suggested in textbooks.

For the case of other LC cells, an effect of achieving a particularly wide viewing angle when applying slight deviations from textbook-like precisely parallel (0°) and precisely perpendicular (90°) alignments has been discussed in US 2012/0002121 A1.

The first common lateral direction, however, is usually selected to be parallel or perpendicular to the rubbing direction of the first cell, in particular within 6° or rather within 2°. In case the rubbing direction at a first of the two laterally extended sides of the first cell and a rubbing direction at a second of the two laterally extended sides of the first cell are at an angle (i.e. not precisely parallel aligned), the mentioned parallelism and perpendicularity, respectively, refers to a direction bisecting an acute angle formed between the two.

For the second common lateral direction and the second cell applies, in analogy, the same.

In one embodiment, the first electrode structure of the first cell predominantly comprises, and in particular predominantly consists of, a plurality of electrically separate electrodes which are stripe-shaped, the stripes running along a lateral direction perpendicular to the first common lateral direction, and the first electrode structure of the second cell predominantly comprises, and in particular predominantly consists of, a plurality of electrically separate electrodes which are stripe-shaped, the stripes running along a lateral direction perpendicular to the second common lateral direction.

In one embodiment with three LC cells, one of the LC cells is TN cell and the other two cells are FFS cells of the herein described kind, in particular wherein the two FFS cells are designed and aligned with respect to each other like herein described for a filter comprising two FFS cells. The TN may in particular be arranged between the two FFS cells.

In another embodiment with three LC cells, two of the LC cells are TN cells and the other cell is an FFS cells of the herein described kind. The FFS cell may in particular be arranged between the two TN cells.

TN cells tend to make possible a particularly fast switching.

FFS cells of the described kind tend to make possible a particularly wide polar angle contrast distribution.

The invention concerns also a filter cassette, namely a filter cassette comprising an electro-optical glare protection filter as described in the present patent application. In particular, the filter cassette also comprises a source of electrical energy and/or at least one light-sensitive detector.

The invention also concerns a glare protection unit for a glare protection device, in particular for a portable glare protection device, wherein the glare protection unit comprises an electro-optical glare protection filter as described in the present patent application or a filter cassette as described in the present patent application.

The glare protection unit may in particular also comprise a face shield for protecting a wearer's face, wherein the electro-optical glare protection filter is arranged in an opening of the face shield.

And, the invention also concerns a welder protection device comprises an electro-optical glare protection filter as described in the present patent application or a filter cassette as described in the present patent application.

In particular, the welder protection device is wearable and/or comprises a face shield for protecting a wearer's face, wherein the electro-optical glare protection filter is arranged in an opening of the face shield.

Further embodiments and advantages emerge from the dependent claims and the figures.

Below, the invention is described in more detail by means of examples and the included drawings. The figures show schematically:

FIG. 1 a polar contrast diagram for 90° crossed polarizer and analyzer;

FIG. 1a a schematized illustration of orientation details for FIG. 1;

FIG. 2 a polar contrast diagram for a single TN liquid crystal (LC) cell;

FIG. 2a a schematized illustration of orientation details for FIG. 2;

FIG. 3 a polar contrast diagram for a filter comprising two TN LC cells;

FIG. 3a a schematized illustration of orientation details for the first LC cell of FIG. 3;

FIG. 3b a schematized illustration of orientation details for the second LC cell of FIG. 3;

FIG. 4 a polar contrast diagram for a filter comprising two LTN LC cells;

FIG. 4a a schematized illustration of orientation details for the first LC cell of FIG. 4;

FIG. 4b a schematized illustration of orientation details for the second LC cell of FIG. 4;

FIG. 5 a schematized side view of a twisted-nematic (TN) LC cell;

FIG. 6 a schematized side view of an in-plane switching (IPS) LC cell;

FIG. 7 a schematized illustration of an electrode structure of an FFS cell, in a view onto the cell plane (negative dielectric liquid);

FIG. 7a a schematized illustration of an FFS cell with interdigital electrode lines, in a side view;

FIG. 7b a schematized illustration of an FFS cell with electrode structures in different distances to the LCs, in a side view;

FIG. 8a a schematized illustration of interdigital electrode lines, in a side view;

FIG. 8b a schematized illustration of electrode structures in different distances to the LCs, in a side view;

FIG. 8c a schematized illustration of electrode structures with alternatingly arranged electrode lines in different distances to the LCs, in a side view;

FIG. 9 a schematized illustration of electrode structures of an FFS cell, in a view onto the cell plane;

FIG. 10a a schematized illustration of an LC-based filter with segmented first electrode structure and a second electrode structure for generation of a two-domain LC alignment, in a view onto the cell plane;

FIG. 10b a schematized illustration of an LC-based filter with segmented first electrode structure and a second electrode structure for generation of a two-domain LC alignment, in a view onto the cell plane;

FIG. 11 a schematic illustration of a filter comprising the two filters of FIGS. 10a and 10b and a control unit;

FIG. 12 a simulation of a polar contrast diagram for a filter comprising the two filters of FIGS. 10a and 10b.

The described embodiments are meant as examples or for clarifying the invention and shall not limit the invention.

FIG. 1 shows a polar contrast diagram for two polarizers which are arranged such that their transmission directions are rotated by 90° with respect to each other. In order to distinguish two polarizers, they are frequently referred to as polarizer and analyzer.

As usual in such polar contrast diagrams, the center corresponds to polar angle theta of a viewing direction being 0° (θ=0°), while theta increases with increasing (radial) distance from the center. And different radial directions in the diagram correspond to different azimuthal angles phi (Φ) of the viewing direction.

An opacity of the filter, i.e. he light attenuation for light incident on the filter in a certain direction (characterized by theta and phi), is encoded in a shade of gray at the corresponding spot in the polar contrast diagram. Please note that the original grayscale polar diagrams were rastered for the present patent application.

FIG. 1a is a schematized illustration of orientation details for FIG. 1. Reference symbols P and A designate the orientation of the transmission axes of the polarizer and the analyzer, respectively, of FIG. 1.

FIG. 1 shows how narrow the polar contrast pattern is which is obtained merely by 90° crossed polarizer and analyzer.

FIG. 2 shows a polar contrast diagram for a single liquid crystal (LC) cell, more particularly for a twisted nematic (TN) LC cell. FIG. 2a schematically illustrates orientation details for FIG. 2. Reference symbols P and A designate the orientation of the transmission axes of the polarizer and the analyzer, respectively, of the LC cell of FIG. 2; $R_P$ and $R_A$ designate the rubbing directions of the LC cell of FIG. 2, at the cell wall next to the polarizer and at the cell wall next to the analyzer, respectively. The LC cell of FIG. 2 is in E-mode.

The polar angle contrast distribution of FIG. 2 is substantially wider than the one of FIG. 1. The best viewing angle for the LC cell of FIG. 2, i.e. the azimuthal direction for which the light attenuation is maximal, is indicated by the dotted rectangle in FIG. 2a. The curved circle in FIG. 2a illustrates the levorotary twisting of the LC cell of FIG. 2.

FIG. 3 shows a polar contrast diagram for an electro-optic filter comprising two LC cells, more particularly two TN LC cells. FIG. 3a schematically illustrates orientation details of the first LC cell (front cell) of FIG. 3 (having index 1), and FIG. 3b schematically illustrates orientation details of the second LC cell (back cell) of FIG. 3 (bearing index 2). Reference symbols P1, P2 and A1, A2 designate the orientation of the transmission axes of the polarizer and the analyzer, respectively, of the first and second LC cells of FIG. 3, respectively. $R_{P1}$, $R_{P2}$ and $R_{A1}$, $R_{A2}$ designate the rubbing directions of the first and second LC cells of FIG. 3, respectively, at the cell wall next to the polarizer and at the cell wall next to the analyzer, respectively. Both LC cells of the filter of FIG. 3 are in O-mode.

FIG. 3 illustrates the levorotary-dextrorotary twisting combination of two liquid crystal displays forming a true two-domain transmissive shutter element. Still, one clearly recognizes deficiencies of the optical anisotropy of TN displays, in particular if compared to simple isotropic passive welding filters.

The positive optical anisotropy of the homeotropically aligned middle layer of the LCs in TN cells generates elliptically polarized light in the on-state which is not completely suppressed by the analyzer. And a molecular alignment tilt deficiency of a boundary layer close to the cell walls creates further unwanted birefringence. These effects are particularly pronounced at larger polar angles theta, i.e. at oblique angles of incident light.

Figures 4, 4A:
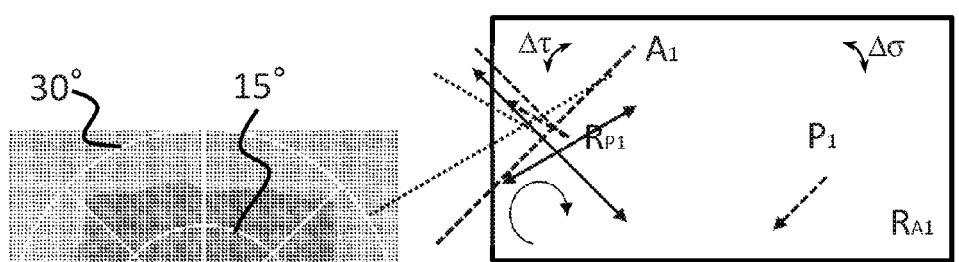

FIG. 4 shows in the same way as FIG. 3 a polar contrast diagram for a filter comprising two TN LC cells, wherein, however, both cells are Low-Twist Nematic (LTN) cells and at the same time also Uncrossed Polarizer Twisted Nematic (UPTN) cells.

Figure 4B:
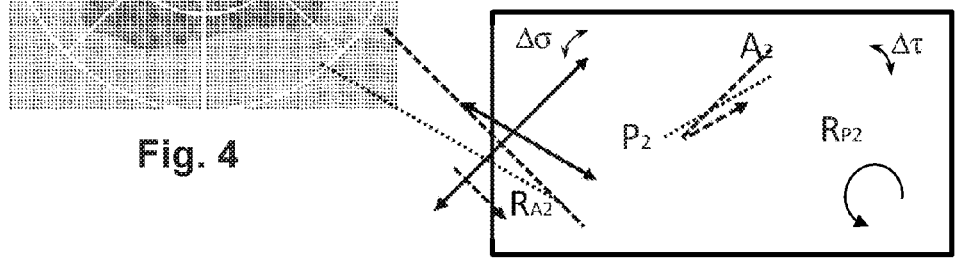

FIGS. 4a, 4b shows in the same way as FIGS. 3a, 3b orientation details for the first and second LC cells, respectively, of FIG. 4.

UPTN cells distinguish over common TN cells in the orientation of the polarizer with respect to the analyzer. Instead of selecting precisely 90°, a UPTN cell has an angle between the transmission axes of the polarizer and the analyzer deviating from 90° by several or at least a couple of degrees, as is illustrated in FIGS. 4a, 4b by angle Δσ. Furthermore, in the cells of the filter belonging to FIG. 4, the rubbing directions for the polarizers ($R_{P1}$, $R_{P2}$) are not aligned perpendicularly to each other, but deviate from that 90° orientation by an angle Δτ, cf. FIGS. 4a and 4b. And similarly, the polarizer directions P1, P2 are not aligned perpendicularly to each other.

Both cells of the filter are in O-mode configuration.

The simulation shown in FIG. 4 demonstrates the possibility to achieve a strongly enhanced contrast distribution and thus a relatively wide contrast distribution by means of a filter comprising the described two LTN/UPTN LC cells.

Figure 5:
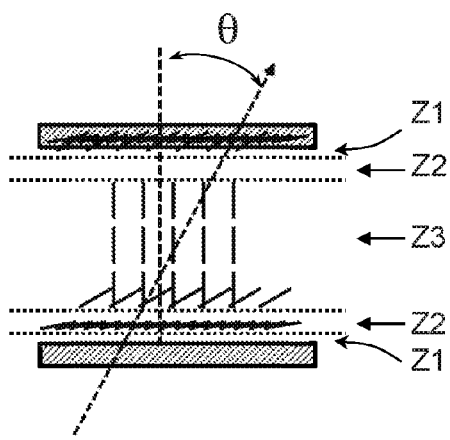
Figure 6:
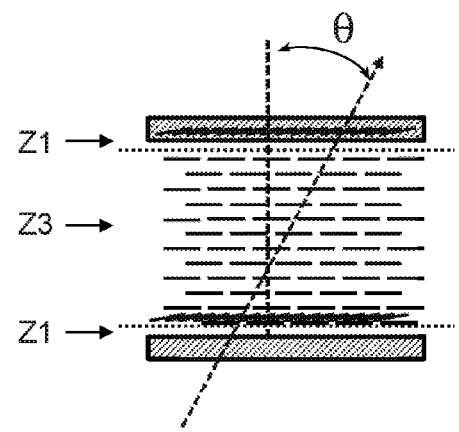

FIG. 5 is a schematized side view of a TN LC cell, and FIG. 6 is a schematized side view of an in-plane switching (IPS) LC cell. In IPS cells, the directors of the LCs (at least of the majority of the LCs) remain substantially within the cell plane. The lines between the cell walls symbolize the directors of the LCs. For the sake of clarity, electrodes are not drawn in FIGS. 5, 6.

In zone Z3 in FIGS. 5 and 6, the mid-layer tilt (or mid-range tilt) of the LCs is illustrated, which is homeotropic in case of the TN LC cell (FIG. 5) and in-plane in case of the IPS cell (FIG. 6), and in zones Z1 in FIGS. 5 and 6, the pre-tilt of the LCs due to the rubbing is illustrated. In Zone Z2 in FIG. 5, the molecular alignment tilt present in TN LC cells is illustrated As is clear from comparing FIGS. 5 and 6, TN cells (FIG. 5) produce orders or magnitude more elliptically polarized light than an IPS cell (FIG. 6) usually does. And elliptical polarization is responsible for the generation of light leakage in LC-based filters under oblique viewing angles (large polar angle theta). This effect is usually undesired because it substantially reduces the polar angular contrast performance.

However, in glare protection applications, e.g., in welding applications, it is usually not desirable to use IPS LC cells (FIG. 6) working in the normally black (NB) mode, because for glare protection filters, it is of importance to be able to darken the filter very quickly, while the time required for making the filter transmissive is not crucial and may take more time; and the LC rearrangement process which is enforceable by application of voltages (in particular including short-time overdrive voltages) may be much faster than the (relaxation) processes occurring when switching off the LC filter. Thus, a normally white (NW) mode LC-based filter is usually preferred in glare protection applications.

As an improved LC cell, in particular for use in glare protection applications, it is therefore suggested to provide a two-domain IPS cell operating in NW mode.

The provision of two domains (and thus of two types of areas, wherein in each of them, the in-plane alignment of the LCs is along a different azimuthal direction) results in an improved polar contrast distribution and can be achieved by selecting a suitable electrode configuration.

Figure 7:
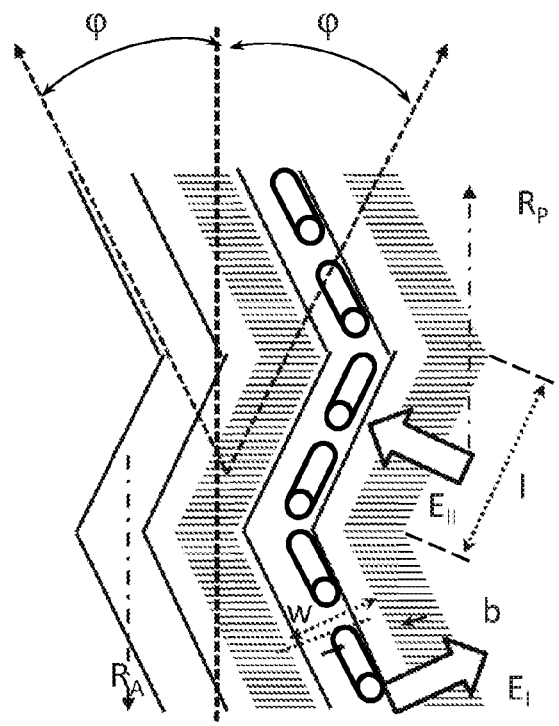
Figure 7A:
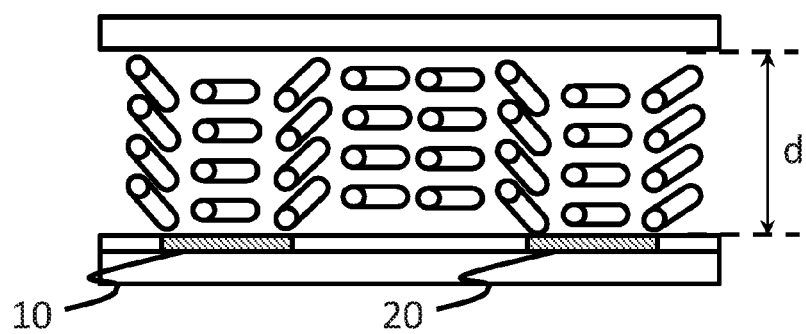
Figure 7B:
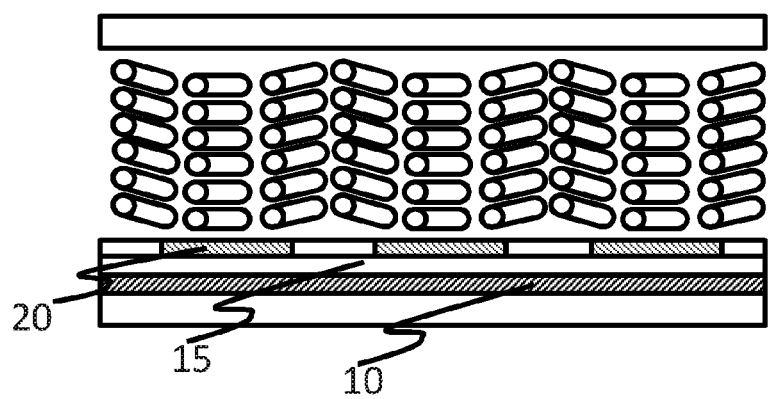

In particular, one of two electrode structures of the LC cell (also referred to as second electrode structure—roughly corresponding to what often simply is referred to as "electrode", in contrast to "common") can have a zigzag shape, e.g. as schematically illustrated in FIG. 7. The tube-like symbols in FIG. 7 symbolize the LCs (with their director along the tube direction) aligned in the on-state, negative dielectric anisotropy assumed. FIGS. 7a, 7b show a cross section of an LC cell with interdigital electrode lines (7a) as compared to an FFS cell (7b) with electrode structures in different distances to the LCs, clearly indicating the reduced vertical tilt of the molecules of the at the edges of the electrodes. The advantage of the reduced vertical tilt is a more homogeneous transmission characteristic.

The hatched portions represent sections of the illustrated electrode structure. The two open arrows labelled $E_I$ and $E_{II}$, respectively, illustrate the alternating electric field directions in the two domains.

The LC cell in FIG. 7 is anti-parallel rubbed (cf. the illustrated rubbing directions $R_P$ and $R_A$), wherein the zigzag-shaped electrode lines (of which only two are illustrated in FIG. 7) are extended along a common (azimuthal) direction which is parallel to the rubbing directions. Each of the electrode lines of the illustrated electrode structure of FIG. 7 can be understood as being composed of several concatenated chevrons, wherein a length of one of the two legs of the chevrons has a length 1 and a width b, and a distance between neighboring chevrons (and thus between neighboring electrode lines) is designated w, also referred to as gap width (not to be confused with the width of the cell gap).

Typical values are: b between 0.1 μm and 3 μm; w between 0.5 μm and 4 μm and 1 between 0.5 μm and 10 μm. An angle φ between chevron legs and the rubbing directions typically amounts to between 30° and 60°, e.g., 45°.

The first electrode structure (very roughly corresponding to what often simply is referred to as "common") may be structured and arranged with respect to the second electrode structure in various ways. Examples are illustrated in FIGS. 7a, 8a, in FIGS. 7b, 8b and in FIG. 8c.

FIG. 7a is a schematized illustration of an FFS cell in a side view, the LC cell having interdigital electrode lines. In this case, electrode lines of the first electrode structure 10 and electrode lines of the second electrode structure 20 are alternatingly placed in a row. Both electrode structures 10, 20 thus have the same distance to the volume in which the LCs are present. FIG. 7a also illustrates very schematically the orientations of the LCs, and shows also the width d of the cell gap.

FIG. 8a is a schematized illustration of interdigital electrode lines, in a side view, wherein the electrode polarities (+,−) and the electric field lines ("E") are symbolized, too.

FIG. 7b is a schematized illustration of an FFS cell in a side view, the LC cell having electrode structures at different distances to the LCs. In this case, the first electrode structure 10 is further distant from the volume containing the LCs than the second electrode structure 20. Between the first and second electrode structures 10, 20, an electrically insulating layer 15 (also referred to as passivation layer) is arranged. FIG. 7b also illustrates very schematically the orientations of the LCs.

FIG. 8b is a schematized illustration of first and second electrode structures 10, 20 as illustrated in FIG. 7b, also in a side view, wherein the electrode polarities (+,−) and the electric field lines ("E") are symbolized, too, in FIG. 7b. Further below (cf. FIGS. 9, 10a and 10b), further details of a more specific embodiment of a first electrode structure are described.

FIG. 8c is a schematized illustration in a side view of electrode structures 10, 20 with alternatingly arranged electrode lines in different distances to the LCs, wherein the electrode polarities (+,−) and the electric field lines ("E") are symbolized, too.

The electric field has a particularly high percentage of electric field components aligned parallel to the cell plane (the cell plane being perpendicular to the drawing plane in FIGS. 7a, 7b, 8a, 8b and 8c) in the cases illustrated in FIGS. 7b, 8b and 8c. Therein, the percentage of electric field components aligned parallel to the cell plane ("horizontal E-components") is higher for the electrode structures illustrated in FIGS. 7b and 8b than for the electrode structures illustrated in FIGS. 8a and 8c. A particularly high percentage of horizontal E-components usually leads to an overall increased light efficiency of the filter, since the in-plane twist of the LCs is thereby supported.

It turned out that an improved dynamic switching speed performance of the filter may be achieved if the first electrode structure 10 is segmented—instead of being merely one single full-area electrode.

The provision of a first electrode structure 10 comprising several separate electrodes makes possible to apply different electrical potentials in different (lateral=horizontal) sections of the LC cell.

FIG. 9 is a schematized illustration in a view onto the cell plane of a first electrode structure and of a second electrode structure of an FFS cell. The first and second electrode structures may be aligned as described for FIGS. 7b, 8b. The second electrode structure has zigzag lines like illustrated in FIG. 7 and is thus suited for producing two-domain LC alignments. In addition to the zigzag electrode lines, the second electrode structure comprises electrode sections which constitute an outer frame within which the zigzag electrode lines are located.

The first electrode structure in FIG. 9 is segmented, more particularly segmented so as to comprise several separate electrodes 12, 12', 12", . . . (or electrode stripes 12, 12', 12", . . . ) which extend along a direction perpendicular to the common (azimuthal) directions along which the zigzag-shaped electrode lines of electrode structure 20 are extended, wherein neighboring electrode stripes are separated by very small gaps such as thin separation lines 11. Holding the electrode stripes 12, 12', 12", . . . at different electrical potentials (with respect to the second electrode structure 20) can make it possible to create a particularly homogenous electrical field distribution across the filter, in particular by at least partially compensating for field strength variations due to sheet resistance effects of the electrode lines of the second electrode structure (which are very long in relation to their width b). These effects are particularly pronounced under dynamic conditions. Thus, compensations achievable by the segmented, e.g., multi-stripe-shaped, first electrode structure can be valuable for achieving a particularly uniform transmittance of the filter and for achieving a particularly homogenous switching behavior of the filter, which again may result in a higher switching speed of the filter.

An alternative to the provision of stripe-shaped electrodes as illustrated in FIG. 9 would be, e.g., to provide a two-dimensional array of electrodes (electrode grid).

An alternative to the provision of zigzag-shaped electrode lines having a common (azimuthal) direction parallel to lateral borders of the LC cell, i.e. at 0° and 90°, respectively, to the (mutually perpendicular) lateral borders of the LC cell, as illustrated in FIG. 9 would be to have them aligned at an angle of about 45° to the lateral borders of the LC cell (not illustrated in FIG. 9). In this case, the other elements of the LC cell illustrated in FIG. 9 are, of course also oriented accordingly.

Figure 10A:
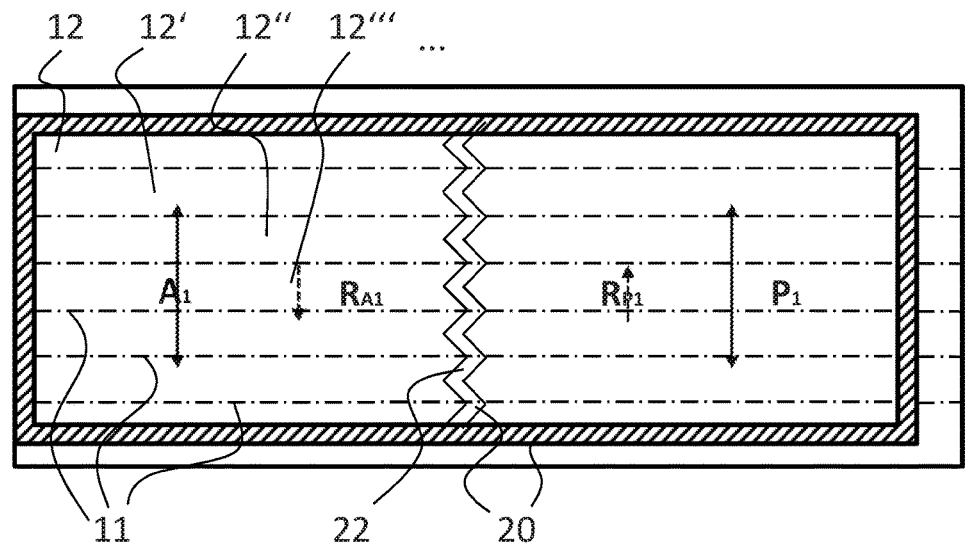
Figure 10B:
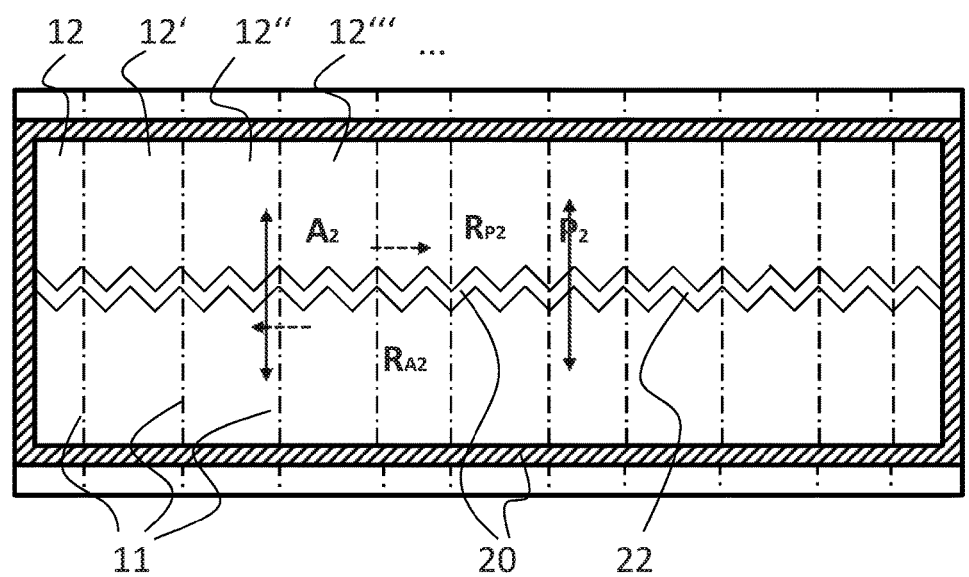

FIGS. 10a and 10b each illustrate an LC-based filter with segmented first electrode structure and a second electrode structure 20 for generation of a two-domain LC alignment.

The second electrode structure 20 is arranged closer to the LCs-containing volume of the respective LC cell than the first electrode structure, e.g., as illustrated in FIGS. 7b and 8b.

The second electrode structure 20 is structured as explained for FIG. 9, but in FIGS. 10a, 10b, only a single electrode line 22 is drawn for reasons of clarity, but in fact, a multitude of such electrode lines (aligned parallel to each other) is present in the second electrode structure 20, cf. also FIG. 9 in which two such electrode lines are shown while only a portion of the outer frame is shown.

References 12, 12', 12", 12'" designate different ones of the separate electrodes of the first electrode structure; the dash-dotted lines indicate separation lines 11 separating neighboring ones of the separate electrodes.

In order to obtain a further improved filter, two LC cells can be stacked upon each other. One of the two LC cell based filters of FIG. 10a and FIG. 10b, respectively, may be combined with another filter, in particular with another LC cell based filter, i.e. with a second LC cell based filter.

The second LC cell based filter may be, e.g., a TN cell based filter.

However, it is also possible to combine the two filters illustrated in FIGS. 10a and 10b, in particular in the orientation in which they are drawn in these Figures. This way, a four-domain LC cell based filter is obtained. Such a filter can have a particularly good polar contrast distribution. The filter can be a true four-domain LC cell based filter. Therein, it is possible to have the zigzag-shaped electrode lines and the separate electrodes of the first electrode structure aligned parallel to the lateral border of the respective LC cell, for both LC cells, as illustrated in FIGS. 10a, 10b. But it is also possible to have them aligned at an angle, e.g., at an angle of between 30° and 60°, e.g., at 45°, with respect to the lateral borders of the respective LC cell.

It is in particular possible to provide that the separate electrodes of the first electrode structure of one of the LC cells are aligned perpendicularly to the separate electrodes of the first electrode structure of the other of the LC cells.

Figure 11:
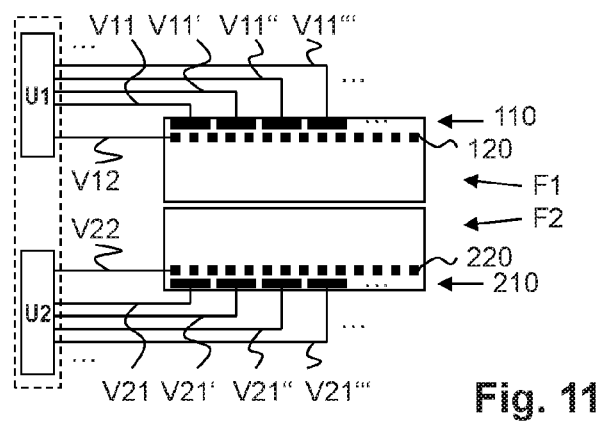

FIG. 11 illustrates such a filter in a strongly schematized way, partially in a side view. The LC cell (or filter) illustrated in FIG. 10a may be, e.g., the LC cell indicated at F1, and the LC cell (or filter) illustrated in FIG. 10b may be, e.g., the LC cell indicated at F2. The first electrode structure of cell F1 is designated 110, and the first electrode structure of cell F2 is designated 210; the second electrode structure of cell F1 is designated 120, and the second electrode structure of cell F2 is designated 220.

In FIG. 11, it is visible that the first electrodes 110, 210 are segmented, so as to make possible to apply different electric potentials to them as explained above. It is of course possible to position the electrode structures in positions different from those illustrated in FIG. 11, e.g., such that they are both on those sides of the cells F1, F2 which are facing each other.

Two voltage supplies U1, U2 are provided in the embodiment of FIG. 11 which make possible to hold the first and second electrodes at suitable electrical potentials V12 and V22 for the second electrode structures 120 and 220, respectively and the various electrodes of the first electrode structures 110, 210 at suitable electrical potentials V11, V11', V11", ... and V21, V31', V41", ..., respectively. Of course, it is possible to provide a single voltage supply for all the voltages, as indicated by the dashed rectangle in FIG. 11.

Of course, for a single FFS cell, an embodiment corresponding to the lower or to the upper half of FIG. 11 can be used.

In FIGS. 7, 9, 10a, 10b, it is typically assumed that the LCs in the corresponding LC cells have a negative electrical anisotropy ($\Delta\varepsilon<0$). However, it is also possible to operate such LC cells with LCs having a positive electrical anisotropy ($\Delta\varepsilon<0$).

Figure 12:
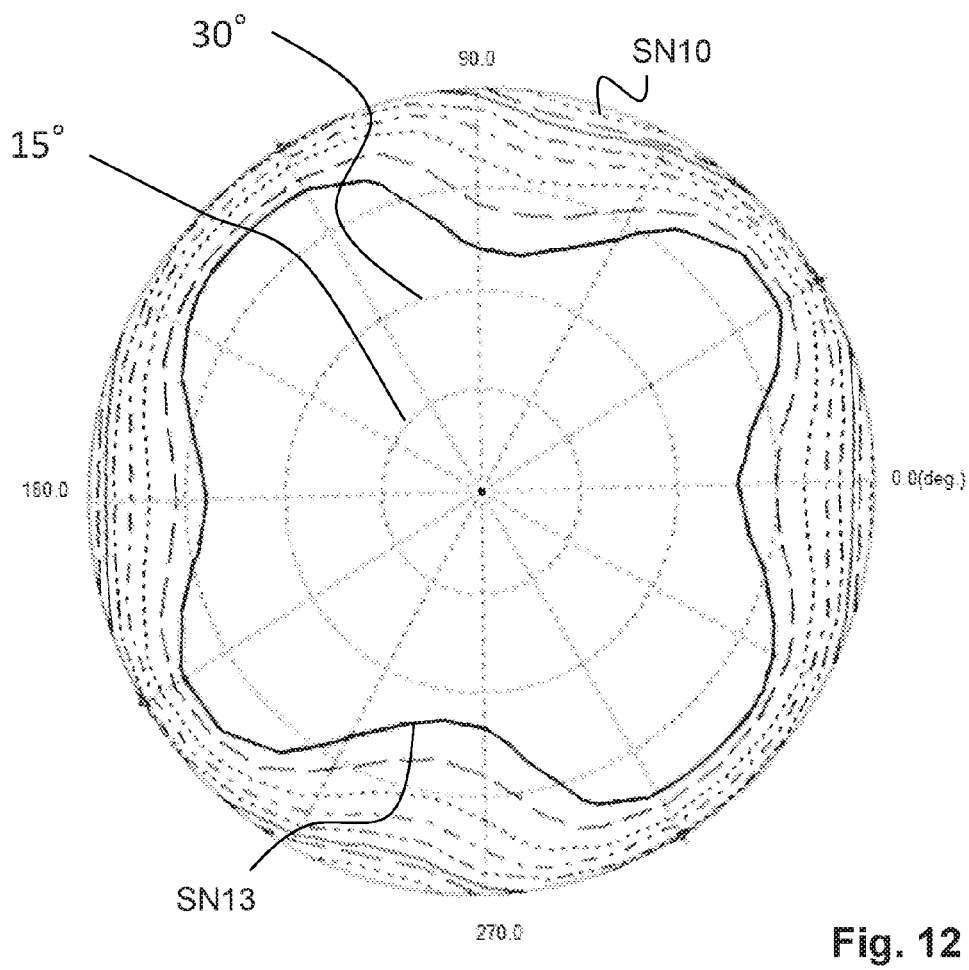

FIG. 12 shows a simulation of a polar contrast diagram for such a filter comprising the two filters illustrated in FIGS. 10a and 10b stacked upon each other, e.g., as illustrated in FIG. 11. The light attenuation (or filter opacity) is visualized in FIG. 12 by lines at which identical attenuation is present (and not in grayscale like in FIGS. 1-4). As indicated, at the inner-most (solid) line, an attenuation corresponding to the SN13 standard ("shade number 13") is achieved, and at the outer-most dashed line, an attenuation corresponding to the SN10 standard ("shade number 10") is achieved. Thus, it is clear that the proposed four-domain filter can make it possible to achieve a strong light attenuation with a very homogeneous polar contrast distribution. It is to be noted that in the simulation of FIG. 12, the above-discussed deliberate deviations from exactly parallel and exactly perpendicular orientations (cf., e.g., FIGS. 4a, 4b) are not included. Accordingly, the achievable contrast distribution (by including said deliberate deviations) is even better than what is shown in FIG. 12.

In case the cell height (thickness, extension of the LC-containing volume in vertical direction, often also referred to as cell gap width d) and the birefringence of the LCs is not sufficient for achieving a 180° phase retardation of the light on its way through the LC-containing volume, an a-plate or other retarder (or rather two a-plates or other retarders, in particular a positive one and a negative one, e.g. $\pm\lambda/6$) can be provided in the LC cell, so as to be able to increase a light efficiency of the filter.

It is also possible to combine three LC-based filters in an electro-optical glare protection filter, in particular one of the described FFS cell based filters and two TN cell-based ones or one TN cell-based filter and two of the described FFS cell based ones (not illustrated).

The invention claimed is:

1. An electro-optical glare protection filter, comprising a liquid crystal cell referred to as first cell, the first cell being an FFS cell, wherein an FFS cell is a laterally extended liquid crystal cell defining a volume between two laterally extended sides, the volume containing liquid crystals and having, in a vertical direction perpendicular to lateral directions, a thickness being smaller than an extension of the volume in any lateral direction, the FFS cell comprising a first electrode structure and a second electrode structure, which are arranged to change an orientation of the liquid crystals in the volume when a voltage is applied between them, wherein both, the first and the second electrode structure, are present at the same laterally extended side of the volume.

2. The filter according to claim 1, wherein the first electrode structure comprises a plurality of electrically separate electrodes.

3. The filter according to claim 1, wherein a lateral area covered by the first electrode structure amounts to at least 90%, in particular at least 95%, of an area of any of the two laterally extended sides.

4. The filter according to claim 2, comprising a drive circuit for producing at least a first and a second drive voltage, wherein the drive circuit is connected to the first and second electrode structures for applying the first drive voltage between the second electrode structure and a first one of the plurality of electrically separate electrodes and for applying the second drive voltage between the second electrode structure and a second one of the plurality of electrically separate electrodes, in particular wherein a minimum drive voltage for application between any one of the electrically separate electrodes of the first electrode structure and the second electrode structure amounts to at least 2.4 V, more particularly to at least 12 V, and wherein a difference between any two drive voltages applied between any one of the plurality of electrically separate electrodes and the second electrode structure amounts to at most 0.4 V, in particular to at most 8 V.

5. The filter according to claim 1, wherein the second electrode structure comprises an electrode comprising a multitude of areas of a first type and a multitude of areas of a second type, wherein each first-type area comprises a plurality of electrode sections of the second electrode structure which run along a first lateral direction, and wherein each second-type area comprises a plurality of electrode sections of the second electrode structure which run along a second lateral direction, different from the first lateral direction.

6. The filter according to claim 5, wherein an angle between the first lateral direction and the second lateral direction amounts to between 60° and 120°, in particular to between 80° and 100°.

7. The filter according to claim 1one of claims 1, wherein the second electrode structure comprises an electrode comprising a plurality of zigzag-shaped electrode lines which are aligned parallel to each other, in particular wherein each of the electrode lines is composed of a multitude of like chevrons concatenated along a specific lateral direction, more particularly wherein the electrode comprises a plurality of electrode lines, wherein a first one of the electrode lines is obtainable by concatenating a multitude of parallel-aligned like chevrons along the specific lateral direction, and wherein the other electrode lines are obtainable by copying the first electrode line and shifting it in a lateral direction perpendicular to the first electrode line.

8. The filter according to claim 7, wherein each chevron consists of two mutually angled legs, wherein for each chevron, a width of the legs of the chevron is between 0.5 µm and 4 µm, and a gap width between neighboring electrode lines is between 0.5 µm and 4 µm, and in particular wherein the legs have a length of between one time and five times the width of the respective leg.

9. The filter according to claim 1, wherein the first cell is anti-parallel rubbed and
in a first case: P-buffed and in E-Mode;
or is
in a second case: X-buffed and in O-Mode.

10. The filter according to claim 9, wherein
in the first case: the specific lateral direction is aligned parallel to a rubbing direction of the first cell;
or
in the second case: the specific lateral direction is aligned perpendicularly to the rubbing direction.

11. The filter according to claim 1, wherein the first cell comprises an electrically insulating layer, wherein the first electrode structure is located on a side of the electrically insulating layer facing away from the volume, whereas the second electrode structure is located on a side of the electrically insulating layer facing towards the volume, in particular wherein the first electrode structure is located at a distance from the volume larger than a distance of the second electrode structure from the volume.

12. The filter according to claim 1, wherein the liquid crystals in the first cell have negative dielectrical anisotropy.

13. The filter according to claim 1, wherein the first cell comprises, in addition, at least one retarding element, in particular at least one uniaxial retarder, for example one or two a-plates, in particular wherein a retardation value of the the at least one retarding element amounts to be positive or negative in value, the absolute value ranging between 60 nm and 110 nm.

14. The filter according to claim 1, comprising, in addition, a liquid crystal cell referred to as second cell, in particular wherein the first and second cells are stacked with their respective vertical directions coinciding.

15. The filter according to claim 14, wherein the second cell is a twisted nematic liquid crystal cell.

16. The filter according to claim 14, wherein the second cell is an FFS cell.

17. The filter according to claim 16, wherein
the first cell is anti-parallel rubbed and P-buffed and in E-Mode, wherein the second electrode structure of the first cell comprises an electrode comprising a plurality of electrode lines each of which is composed of a multitude of chevrons concatenated along a first common lateral direction;
the second cell is anti-parallel rubbed and X-buffed and in O-Mode, wherein the second electrode structure of the second cell comprises an electrode comprising a plurality of electrode lines each of which is composed of a multitude of chevrons concatenated along a second common lateral direction;
wherein a rubbing direction of the first cell is perpendicular to a rubbing direction of the second cell, and wherein the first common lateral direction is parallel to the rubbing direction of the first cell, and wherein the second common lateral direction is parallel to the rubbing direction of the second cell,
in particular wherein at least one of
the perpendicular alignment of the rubbing direction of the first cell to the rubbing direction of the second cell deviates from 90° by an angle of between 1° and 8°;
the parallel alignment of a rubbing direction at a first of the two laterally extended sides of the first cell to a rubbing direction at a second of the two laterally extended sides of the first cell deviates from 0° by an angle of between 1° and 8°;
the parallel alignment of a rubbing direction at a first of the two laterally extended sides of the second cell to a rubbing direction at a second of the two laterally extended sides of the second cell deviates from 0° by an angle of between 1° and 8°;
a parallel alignment of a polarizing direction of a polarizer at a first of the two laterally extended sides of the first cell and a polarizing direction of an analyzer at a second of the two laterally extended sides of the first cell deviates from 0° by an angle of between 1° and 8°;
a parallel alignment of a polarizing direction of a polarizer at a first of the two laterally extended sides of the second cell and a polarizing direction of an analyzer at a second of the two laterally extended sides of the second cell deviates from 0° by an angle of between 1° and 8°.

18. The filter according to claim 17, wherein the first electrode structure of the first cell predominantly comprises, and in particular predominantly consists of, a plurality of electrically separate electrodes which are stripe-shaped, the stripes running along a lateral direction perpendicular to the first common lateral direction, and the first electrode structure of the second cell predominantly comprises, and in particular predominantly consists of, a plurality of electrically separate electrodes which are stripe-shaped, the stripes running along a lateral direction perpendicular to the second common lateral direction.

19. A filter cassette comprising an electro-optical glare protection filter according to claim 1, in particular comprising a source of electrical energy and at least one light-sensitive detector.

20. A glare protection unit for a glare protection device, in particular for a portable glare protection device, wherein the glare protection unit comprises an electro-optical glare protection filter according to claim 1, wherein the glare protection unit comprises a face shield for protecting a wearer's face, the electro-optical glare protection filter being arranged in an opening of the face shield.

21. A welder protection device comprising an electro-optical glare protection filter according to claim 1, wherein the welder protection device is wearable and/or wherein the welder protection device comprises a face shield for protecting a wearer's face, the electro-optical glare protection filter being arranged in an opening of the face shield.

* * * * *